United States Patent [19]

Berglund et al.

[11] Patent Number: 4,752,571
[45] Date of Patent: Jun. 21, 1988

[54] METHOD FOR DETERMINING CERTAIN BACTERIAL POLYPEPTIDES AND ANTIBODIES DIRECTED AGAINST THEM

[75] Inventors: Asta Berglund; Mats W. Inganäs, both of Uppsala, Sweden

[73] Assignee: Pharmacia AB, Uppsala, Sweden

[21] Appl. No.: 865,853

[22] Filed: May 22, 1986

[30] Foreign Application Priority Data

Jun. 3, 1985 [SE] Sweden ............................ 8502722

[51] Int. Cl.$^4$ ............................................ G01N 33/53
[52] U.S. Cl. .................................... 435/7; 436/518; 436/531; 436/825; 436/826; 436/828
[58] Field of Search ............... 436/518, 531, 828, 825, 436/826; 435/7

[56] References Cited

U.S. PATENT DOCUMENTS

| | | | |
|---|---|---|---|
| 3,966,868 | 6/1976 | Sjöquist et al. | 436/512 |
| 3,995,018 | 11/1976 | Sjöquist et al. | 436/512 |
| 4,409,330 | 10/1983 | Pollard, Jr. | 435/177 |
| 4,469,796 | 9/1984 | Axén et al. | 436/828 |
| 4,471,058 | 9/1984 | Smith et al. | 436/519 |
| 4,590,168 | 5/1986 | Sytkowski et al. | 436/513 |
| 4,617,266 | 10/1986 | Fahnestock | 435/253 |

OTHER PUBLICATIONS

Erntell et al., "Alternative Non-Immune F(ab'-)$_2$-Medicated Immunoglobulin Binding to Group C and G Streptococei" Scand. J. Immunol. 17:201–209 (1983).
Inganäs et al., "Further Characterization of the Alternative Protein-A, Interaction of Immunoglobulins: Demonstration of an Fc-binding Fragment of Protein A Expressing the Alternative Reactivity" Scan. J. Immunol. 14:379–388 (1981).
Kinet, "Ex vivo Perfusion of Plasma Over Protein A Columns in Human Mammary Adenocarcinoma Evidence for a Protein A Leaking by Radio Immunoassay" Eur. J. Clin. Invest. 16:43–49 (1986).
Martin, "Chromatographic Fractionation of Rhesus Monkey (Macaca Mulatta) IgG Subclasses Using DEAE Cellulose and Protein A-Sepharose, J. Immol. Meth., 50 (1982) 319–329.
Langone et al., "Radioimmunoassays for Protein A of Staphylococcus aureus", J. Immunol. Meth., 63 (1983) 145–157.
Dertzbaugh et al., "An Enzyme Immunoassay for the Detection of Staphylococcal Protein A in Affinity-Purified Products", J. Immunol. Meth. 83 (1985) 169–177.
Juarez-Salinas et al., "Binding of IgG to Protein A", Chem. No., 105 (1986) #189332k.

*Primary Examiner*—Christine M. Nucker
*Attorney, Agent, or Firm*—Fred Philpitt

[57] ABSTRACT

Method and means in/for the immunoassay determination of (I) a bacterial polypeptide capable of binding to the Fc protion of an immunoglobulin and/or (II) the high affinity antibody to said polypeptide. The characteristic feature of the method resides in using an antibody directed against the polypeptide and having antibody activity under conditions such that the immunoglobulin potentially binding to the polypeptide will substantially not bind to the polypeptide, and carrying out the immune reaction between the antibody preparation and the corresponding polypeptide epitope under such conditions.

11 Claims, No Drawings

METHOD FOR DETERMINING CERTAIN BACTERIAL POLYPEPTIDES AND ANTIBODIES DIRECTED AGAINST THEM

The invention relates to a method and means for immunologically determining (i) a bacterial polypeptide possessing affinity to the Fc portion of mammalian Ig (i.e. immunoglobulin from mammals), or (ii) an antibody directed against such a polypeptide.

These polypeptides are known to be precipitable by mammalian Ig; the reason for this is believed to reside in that these polypeptides may have a Fab binding capacity in addition to their Fc binding capacity.

The term "bacterial polypeptide" means a polypeptide or protein naturally produced by bacteria or other microorganisms. It comprises also bacterial polypeptides expressed by non-bacterial cells upon application of so-called recombinant DNA techniques.

The concept "polypeptide possessing capacity of Fc binding" (=affinity to the Fc portion of mammalian Ig) comprises both the polypeptide and those fragments and derivatives thereof which have this capacity and/or a Fab binding capacity.

A large number of review articles have been published dealing with this type of polypeptide and its use and whereabouts see for example Langone J J: Adv Immunol 32 /1982/ p. 157-252.

In 1966 it was found that Protein A from S. aureus exhibited Fc binding capacity (Forsgren A & Sjöquist J: J Immunol 17 /1966/ p 822-27). Some years later an analogous protein —viz. Protein G—was discovered in Streptococcus pneumoniae (Kronvall G: J Immunol 111 /1973/ p 1401-06, and Myhre E B & Kronvall G: Infect & Immunity 17 /1977/ p 475-82).

Later on Fc binding polypeptides were detected also in other bacterial species. There are some results indicating that Proteins A and G appear to exhibit structural variations according to species within each respective genus of bacteria. It has been shown during recent years (Inganäs M et al: Scand J Immunol 14 /1981/ p 379-88, and Erntell M et al: Scand J Immunol 17 /1983/ p 201-9) that in addition to their Fc binding capacity these proteins may have an alternative but weak Fab binding capacity. This capacity, called "alternative reactivity", is considered to be independent of any particular class of immunoglobulins. Variations between Igs for these two binding capacities occur between i.a. different species and between Igs originating from different cell clones; the greatest variations have been found in respect of Fab binding capacity. The exact biological significance of these reactivities is not yet known, but it is suspected that they may be relevant with regard to pathogenicity (Forsgren A: Infect & Immunity 2 /1979/ p 672-3, and Forsgren A: Acta Path Microbiol Scand Sect B 80 /1972/ p 564-70).

In actual practice Protein A has been utilized in many different ways, and it is believed that other bacterial polypeptides having Fc binding capacity may potentially be utilized in an analogous manner. In respect of Protein A numerous studies have been made which show that perfusion and recycling of plasma from tumor patients (Terman D S et al: N Eng J Med 305 /1981/ p 1195-) or experimental animals (Terman D S et al: J Immunol 124 /1980/ p 795-, and Science 209 /1980/ p 1257-) over solid-phase-bound Protein A may be conducive to a significant regression of tumors. Because Protein A in itself may give rise to strong biological reactions it is imperative that one should have full control of any potential Protein A leakage during perfusion. It is thus very important that one should be able to sensitively and specifically assay for Protein A contaminations in immunoglobulin-containing preparations.

An assay method serving this purpose has been previously known (Langone J J et al: J Immunol Meth 63 /1983/ p 145-57). The method uses a competitive system in which labeled Protein A and nonlabeled Protein A will compete for chicken anti-Protein A antibody, whereupon the resultant immune complex is precipitated with ammonium sulfate F(ab')₂ rabbit IgG anti-chicken IgG. The utility of this method is however restricted by the phenomenon of interference with sera from animals having an IgG that binds strongly to Protein A (e.g. human IgG and dog IgG). The said method is therefore unsuitable for the characterization of preparations containing immunoglobulins of these animals. Particularly high demands have to be made on the quality of the method in cases where a preparation studied is to be used parenterally.

The aforesaid interference is due to the fact that the IgG of the sample binds to labeled Protein A. This binding capacity is a persistent phenomenon irrespective of whether or not the sample is diluted.

During the priority year two articles describing alternative methods for the determination of Protein A have appeared (Dertzbaugh M T et al; J Immunol Meth 83 /1985/ p 169-78 and Kinet J P et al; Eur J Clin Invest 16 /1986/ p 43-49).

One of the objects of this invention is to provide an assay method minimizing the aforesaid interference of sample serum IgG with said polypeptide in a simple and practical manner. A second object is to provide an assay method having improved precision, sensitivity and selectivity characteristics. A third object is to provide a way of studying leakage in an affinity adsorbent containing the polypeptide as its active substance. A fourth object is to provide antibody preparations which are specific for a polypeptide of the type as here contemplated when the conditions are such that serum immunoglobulins (in the first place human IgG) do not bind to said polypeptide. A fifth object is to provide an assay method for immunoglobulins which via their Fab portion exhibit a strong capacity of binding to the said contemplated type of polypeptide, preferably with an epitope corresponding to the alternative reactivity. "Strong" binding capacity means that the bindings takes place at a pH of below 3.5, these immunoglobulins thus being so-called high affinity antibodies.

The invention constitutes an improvement over known methods for Protein A determinations.

Anti-Protein A antibodies in relation to the alternative reactivity have been studied previously (Inganäs M et al; Scand J Immunol 14 /1981/ p 379-88). However, it was not observed that the preparations then employed exhibited an unusual high antibody activity at pH below 4.

The novel feature of the immunoassay of the invention resides in performing the immune reaction between an epitope of the polypeptide and an antibody directed against it under conditions such that the capacity of the polypeptide of reacting with other immunoglobulins in the sample is suppressed. The antibody employed in the reaction has been chosen such that in the reaction mixture said antibody will react with the polypeptide mainly with its Fab portion.

A large number of general types of immunological assay methods are known per se and potentially useful in the invention.

Immunological assay methods (immunoassay methods) use immune reactants for the formation of an immune complex, the formation of which indicates that an immunological counterpart of an added reactant has been present in a sample. To facilitate quantitation and detection one of the reactants is often added in a labeled form, that is, the reactant is provided with an analytically detectable group. The added amounts of reactants are carefully chosen such that the amount of labeled reactant incorporated in the complex or remaining free, in its uncomplexed state, will be a measure of the species to be assayed for.

According to one classification system, the methods may be classed as being either homogeneous or heterogeneous methods. Homogeneous methods assay for a labeled reactant *without* involving physical separation of complexed (complex-bound) labeled reactant from uncomplexed reactant. Homogeneous methods use markers which will undergo a change in their activity depending on whether or not they are complexed; it is thus possible to measure the signal from a reaction mixture containing the marker in both forms, and to draw conclusions from the value thus obtained as to the amount of the species to be assayed for. Heterogeneous methods involve physical separation of complexed labeled reactant from uncomplexed reactant. In the case of heterogeneous methods there is no requirement that the marker should undergo any changes in activity. The separation is made feasible in that one of the two forms of labeled reactant has been bound or is being bound to a solid phase or other phase which is insoluble in the reaction mixture and readily separable from the liquid phase. The analytically detectable group is then determined in either one of the two phases or in both.

According to a second classification system, the methods may be classed as being either competitive or noncompetitive methods. In a competitive method the arrangement is such that two reactants having a common epitope are made to compete for an insufficient number of homologous binding sites on an immunological counterpart. Usually the systems are chosen such that competition takes place between the species to be assayed for and a variant form thereof which is labeled or bound to a solid phase. The amount that binds to the immunological counterpart is a measure of the species assayed for. In a noncompetitive method, the reactants are chosen such that no competition can occur. Among noncompetitive methods may be noted in particular the so-called "sandwich" systems.

According to a third classification system, the methods may be classed as being either precipitation or non-precipitation methods. In the case of a precipitation method the immune reactions are at first made to proceed in a homogeneous liquid phase whereupon the resultant immune complex is precipitated with the aid of a precipitating agent such as polyethylene glycol, antiserum or solid-phase-bound antibody (but with the antiserum or the solid-phase-bound antibody chosen such that it is not directed against the labeled reactant).

According to a fourth classification system, the methods may be classed according to the marker group employed; the methods are thus radio-, enzyme-, fluorescence-, chemiluminescence-, enzyme-substrate immunological etc. methods.

In immunoassay methods antibodies and antigens may in some cases be replaced by other reactants having biospecific affinity for each other.

At present, with the knowledge gained so far, the invention is preferably performed with heterogeneous-type competitive systems.

It may be noted especially in the context of this invention that suitable competitive systems should utilize competition between labeled and nonlabeled analyte for binding sites on the immunological counterpart of the analyte, said counterpart being optionally bound to solid phase.

The sample to which the invention may be applied may consist of a serum sample or plasma sample. If desired this sample may have been preadsorbed with the species assayed for, as e.g. with Protein A or Protein G in a solid-phase-bound form, such as in an extracorporeal shunt. Also the sample may be an immunoglobulin preparation or some other preparation suspected to contain the species looked for—e.g. the polypeptide or its high affinity antibody.

According to the invention labeled analyte and/or homologous antibody to the polypeptide is/are added to the sample, optionally diluted with a suitable buffer. In subsequent steps further immune reactants may be added, such as for instance antibodies directed against one of the reactants previously added. As regards the antibodies employed in the context of this invention it is suitable that these be either (i) such in which the Fc portion does not react with the polypeptide (labeled or nonlabeled) in a manner interfering with the test or (ii) such in which the Fc portion has been removed or inactivated. The antibodies employed may be for instance the well-defined immunoglobulin fragments Fab, Fab' or F(ab')$_2$. Polypeptide-Ig interference can be avoided also by selecting the antibody from among special classes of immunoglobulins, cell clones and types of animals. The antibody preparations employed have a specificity, affinity, avidity and titer such as required for their use in accordance with the invention. They may take the form of adsorbed preparations, in order to attain a desired degree of specificity. They may be for example an IgG preparation of the antibody. They may take the form of dried preparations, e.g. freeze-dried or spray-dried. The preparation may be one that has been reconstituted in a suitable buffer and accommodated in a hermetically sealed packing which may form part of a test kit.

The anti-Protein A antibody preparation employed possesses specificity against the polypeptide contemplated—preferably against epitopes corresponding to the alternative reactivity. The antibodies of the preparation may be produced by means of immunization and purification in a manner known per se; immunization is carried out by injecting the bacterial polypeptide in a warm-blooded vertebrate together with an adjuvant. Animals commonly employed are birds, for example gallinaceous birds such as chickens, and mammals such as e.g. rats, rabbits, sheep, dogs, horses etc. When an immunization scheme has been carried out antibodies may be recovered from the blood of the animals and—in the case of birds—also from eggs. The antibodies can be IS purified (immunosorbent purified) in a manner known per se, to thus produce the degree of purity required in the particular assay method contemplated. In the context of this invention very good immune responses have been obtained with animals having immunoglobulins of generally a relatively low reactivity (Fab reactivity) against the target bacterial polypeptide. Thus it is advantageous to immunize rabbits or chickens, although other animals too may be useful, such as goats. We have obtained particularly good results in carrying out immunizations with the polypeptide complexed to a heterologous Ig, the Fc portion of which binds strongly to the polypeptide (e.g. Protein A - dog IgG complex).

As an alternative way of proceeding, lymphocytes from animals which have been immunized (e.g. as described above) are used for so-called monoclonal technique (Köhler & Milstein C: Nature 256 /1975/ p 495–7). Monoclonal antibodies of suitable specificity and affinity may be obtained in this manner. Such antibodies may then be used either as so-called simple monoclonals or as composite monoclonals, these latter being mixtures of two or more monoclonal preparations having specificities for different determinants and/or having different affinities.

The term "antibody preparation" according to the invention is of course meant to comprise preparations containing antibody-active fragments (e.g. Fab, F(ab')$_2$ etc.) and derivatives (solid-phase-bound and labeled antibodies).

The antibody preparation to be employed has an affinity constant (expressed as moles/lit.) at least less than that which is characteristic of the relationship between the polypeptide and the corresponding Fc binding immunoglobulin in the sample. If the affinity constant is expressed in liters/mole then the opposite applies. The constants of course have to be compared under relevant conditions, that is, under the conditions appertaining to each respective embodiment of the invention.

The antibody preparation of the invention has an antibody activity which is remarkably little dependent on pH. Thus at a pH of 3.2–3.5 the activity is higher than 30%, e.g. higher than 50%, of the activity at pH 7.4. In particular for the anti-Protein A antibody preparation as used in Example 1, in which the antibody active components are coupled to Sephadex® (Pharmacia AB, Sweden), the following applies: Constant amount of Sephadex® anti Protein A mixed with a constant amount of Protein A at pH 7.4 and pH 3.2; it is then found that the bound activity at pH 3.2 is 50% of that at pH 7.4.

In some embodiments or variant forms of the invention so-called solid-phase-bound antibodies may be employed. Binding antibodies to solid phases are prior art procedures (see for example Wide L: Radioimmunoassay and Related Procedures in Medicine, Vol. I /1978/ IAEA p 143-154). As examples of solid phases may be mentioned particulate hydrophilic matrices which are swellable to form gels but are insoluble in water and which contain OH or NH$_2$ groups (examples are polyamides, polysaccharides, poly(hydroxyalkylacrylates) and corresponding methacrylates etc.). In its insoluble form, the antibody employed is covalently or adsorptively bound to a water-insoluble matrix.

As mentioned above the immune reaction is carried out under conditions such that the immunoglobulins present in the sample will not in any objectionable way bind to the polypeptide or its labeled analog. This means as a rule that the pH has to be below 4; in the cases of Protein A and Protein G, for instance, the pH has to be less than 3.5. The pH must not be so low as to break up the antigen-antibody bond. This means the pH has to be chosen so as to be higher than about 2.7, preferably higher than about 3.0. Suitable buffer systems for pH 2.7–4.0 are those that have a high buffering capacity within that range and will not interfere with the immune reaction. As examples may be mentioned citrate, glycine-HCl and citrate-phosphate buffers. This however does not exclude the use of other agents inhibiting the binding reaction between the Ig of the sample and the polypeptide. The temperature chosen should as a rule be within the range of from 10° to 40° C.

There are various types of substances that may disturbingly interfere with immunological test methods. This is often because they have epitopes directed against or equal to those of the analyte. Thus for instance, the polypeptide, its high affinity homologous antibody, and the corresponding antiidiotype antibody may interfere with each other's determination. A person skilled in the art will evaluate the risk of such interferences experimentally, and also find out how these interferences would affect results of any particular measurement.

The immune reaction between the polypeptide and its antibody is carried out at a pH substantially below the normal pH of 6–9. In the immunosorbent purification procedure desorption is performed at a pH of about 3 or lower—that is, the antigen-antibody bond is broken below about pH 3. The Protein A - IgG complex dissociates at about pH 3–4. The invention is based on our having been able to produce an antibody preparation which is specific against the polypeptide and has antibody activity under conditions in which the general Ig binding capacity of the polypeptide is substantially reduced.

The invention will now be elucidated by means of working examples the purpose of which is solely to illustrate the invention and not, in any way, to limit it.

EXAMPLE 1

Competitive method utilizing labeled Protein A and solid-phase-bound antibody. Preparation of rabbit anti-Protein A.

Three rabbits were immunized by intramuscular injection of a mixture of Protein A (Pharmacia AB, Uppsala, Sweden) and dog IgG (isolated by affinity chromatography on Protein A Sepharose® (Pharmacia AB, Sweden) from dog serum. During a period of seven weeks each animal received three injections of 250 μg Protein A/IgG mixture emulsified in an equal volume of 50% CFA/50% IFA (CFA=Complete Freunds's adjuvant, IFA=Incomplete Freund's adjuvant). A booster injection was given after 18 weeks. Bleedings of rabbits were started from the 20th week onwards (40 ml blood corresponds to 20 ml serum). During the next eight weeks five bleedings were performed on each rabbit. The collected material was pooled and corresponded to 290 ml of anti-Protein A antiserum.

Purification of anti-Protein A 290 ml anti-Protein A antiserum was absorbed on solid-phase-coupled human IgG and rabbit IgG (51 ml and 30 ml column volume respectively). The absorbed antiserum was desalted on Sephadex® G-25 (Pharmacia AB, Sweden), and the Ig fraction was purified by means of ion exchange chromatography on DEAE-Sepharose® CL 6B (Pharmacia AB, Sweden) equilibrated with 0.075M Tris-HCl, pH 8.0. The unretarded fraction was collected and concentrated by ultrafiltration to 116 ml×11.9 mg=1380 mg of Ig. The material was then dialysed against 0.1M acetate buffer, pH 4.5, and digested with pepsin (50:1 w/w) for 16 hours. The Fab'₂ fragment was isolated by gel filtration on Sephadex ® G-100 (Pharmacia AB, Sweden) and gave a total of 757 mg of Fab'₂ anti-Protein A. The fraction of Protein A reactive Fab'₂ fragments was purified by affinity chromatography on Protein A Sepharose ® (Pharmacia AB, Sweden). After desalting on Sephadex ® G-25 (Pharmacia AB, Sweden) the final material consisted of 25.4 mg Fab'₂ anti Protein A. In immunoelectrophoresis the antibody preparation precipitated commercially available Protein A (Pharmacia AB, Sweden). No reactivity was obtained against normal human and dog sera.

Buffer 1

As standard diluent: 0.05M phosphate buffer pH 7.4, 0.5M NaCl, 0.05% Tween ® 20, 0.05% sodium azide.

Buffer 2

For incubation, 0.3M citrate buffer, pH 3.2, 0.05% Tween ® 20.

Standards

Protein A (Pharmacia AB, Sweden) was reconstituted in 1 ml of distilled water. The resultant aqueous solution was diluted with standard buffer to concentrations of 500, 100, 50, 10, 5, and 1 µg Protein A per liter.

Iodination of Protein A

Protein A was iodinated by the Chloramine-T method (Hunter and Greenwood: Nature 194 /1962/ p 495-). The specific activity obtained was approximately 1.94 mBq/ µg Protein A. Concentration 4.5 mg/l.

Sephadex ® antibody complex

Ultrafine Sephadex ® G-25 (Pharmacia, Sweden) having a particle size of 1–10 µm was activated with BrCN (according to Axen R et al: Nature 214 /1967/ p 1302–1304). To 100 mg of activated Sephadex G-25 were coupled 100 µl antiserum (0.39 mg Fab'₂ anti Protein A) according to the method described by Wide L: Acta Endocrinologica suppl 142 /1969/ p 207–221.

Test procedure

To each test tube were added 0.2 ml labeled Protein A (1 ng ¹²⁵I-Protein A), 0.05 ml Protein A standard solution or 0.05 ml undiluted patient's serum, and 0.2 ml of the antibody suspension containing 100 mg/l Sephadex ® with the antibody attached thereto. The antibody suspension was diluted in the citrate buffer as well as the labeled Protein A preparation. All samples (tubes) were run in duplicate. The tubes were shaken for four hours or overnight at room temperature. The particles were washed three times with 0.9% NaCl by centrifugation and aspiration.

Calculation of results

The mean value of the counts for the standard without Protein A ($B_o$) was calculated. The number of counts ($B_x$) for each standard with Protein A was then expressed as percent of $B_o$. The standard curve could then be constructed by semilogarithmically plotting the number of counts of the standards as percent of $B_o$ against the Protein A concentrations. The mean value of the counts of each unknown sample is then expressed as percent of $B_o$; the concentration of Protein A can thus be read off from the standard curve. ($B_x/B_o$)×100 for each standard is set forth in Table 1A. From the standard curve, it is possible to define a lower Protein A detection limit of 1 µg Protein A per liter.

Function of the exemplified test variant in the presence of human IgG

Known amounts of Protein A were added to human plasma and tested in accordance with the above-exemplified variant of the invention. For results see Table 1B. No significant differences were obtained in the slope of the standard curve or in sensitivity, indicating that the presence of large amounts of normal human IgG will not affect the characteristics of the test at pH 3.2.

The test was performed at various different pH levels. Below pH 3.0 no immune reaction occurred. At pH values above 3.5 the labeled Protein A interacts with serum immunoglobulins so that the $B_o$ rapidly decreases to zero (Cp J Immunol Meth 63/1983/ p 145–57).

Plasma from blood donors was adsorbed to Protein A Sepharose ® (Pharmacia AB, Sweden), whereupon adsorbed IgG was released from the adsorbent by progressive stepwise lowering of the pH of the eluent to 4.5, 4.0, 3.5, 3.0 and 2.7–2.8 In the plasma fraction eluted at pH 2.7–2.8 but not above pH 3.0 a factor having an inhibiting effect in the test variant could be detected in the case of 50% of the blood donors. Due to its inhibitory effect the factor gave rise to too high Protein A values. It is highly probable that this is an anti Protein A antibody of high affinity. It should not be present in IgG preparations or other plasma fractions that have been released from or passed through Protein A adsorbents at a pH above the dissociation pH of Protein A - IgG. In other test variants the factor need not inhibit the reaction between Protein A and its antibody. This applies inter alia to systems utilizing an excess of anti Protein A antibody (for example "sandwich" systems).

The above desorption experiment shows that anti Protein A antibodies may be present which bind to Protein A at a pH of about 2.75.

| Tables 1A and 1B | | |
|---|---|---|
| Standard curve for Protein A in serum and buffer system (pH 3.2) in the range of 1–500 µg/l | | |
| Protein A (µg/l) | (A) Buffer system ($B_x/B_o$) % | (B) Serum ($B_x/B_o$) % |
| 1 | 98.3 | 98.0 |
| 5 | 95.1 | 89.5 |
| 10 | 89.0 | 83.5 |
| 50 | 61.2 | 55.5 |
| 100 | 41.4 | 38.5 |
| 500 | 9.6 | 11.5 |

EXAMPLE 2

Double antibody solid-phase method (DASP) for the determination of Protein A

Antobody having specificity for Protein A(Fab'₂ anti Protein A), buffer 1, buffer 2, standards and iodine-labeled Protein A from Example 1 were employed.

2A: Coupling of sheep antirabbit IgG antibodies to BrCN-activated agarose

Agarose beads (0.5–5µ, Pharmacia AB) were BrCN-activated (accordig to Axen R et al: Nature 214 /1967/ p 1302–1304) and subjected to suction on a glass filter funnel. 8 g of activated gel were mixed with 4 mg of sheep antirabbit antibodies in 36 ml of 0.1M NaHCO₃ and incubated on a shaker overnight at +4° C. The reaction mixture was then centrifuged for 10 minutes at 2000×g, and the supernatant was removed by aspiration. This was then followed by washing with 40 ml of 0.1M Tris buffer +1M NaCl, pH 8.1, 10 minutes of centrifugation and aspiration. Incubation with 40 ml of acetate buffer +1M NaCl, pH 4.0, 10 minutes of centrifugation and aspiration. Incubation with 40 ml of 1M ethanolamine-HCl, pH 9.0, 1 hour of centrifugation and aspiration. The aforesaid Tris buffer and acetate buffer washes were repeated twice. Then 40 ml of 0.05M phosphate buffer +1M NaCl +0.01M EDTA +0.05% Tween 20 were added and incubated for 10 minutes. This was followed by centrifugation and aspiration. The phosphate buffer wash was repeated twice. The gel was diluted to 0.3 g/ml in phosphate buffer and sonicated.

2B: Determination of Protein A

To each test tube were added 0.2 ml labeled Protein A (as according to 1) diluted 1000 ×in buffer 2. 0.05 ml of the standard solutions containing 500, 100, 50, 10, 5 and 1 μg/l diluted in human plasma were added to tubes 1-12, and to a number of tubes undiluted patient's serum was added. To all the tubes were added 0.2 ml of the antibody diluted 10,000 ×in buffer 2. The mixture was incubated on a shaker for 4 hours.

2 ml of the diluted gel from 2A diluted 60 × was added and incubated at rest at room temperature for 1 hour. Centrifugation 10 minutes at 3000 revolutions/minute. Decantation. The tubes are placed in a gamma counter. The number of counts per unit time for the standard solutions is calculated as % of the $B_o$ sample and inserted in a lin log diagram from which the amount of Protein A in an unknown test sample can be calculated.

TABLE 2A

Standard curve for Protein A in plasma (pH 3.2) withing the range of 1-500 μg/l.

| Protein A (μg/l) | $(B_x/B_o) \times \%$ |
|---|---|
| 500 | 36.1 |
| 100 | 61.0 |
| 50 | 73.2 |
| 10 | 89.9 |
| 5 | 93.0 |
| 1 | 99.2 |

The invention is set forth in the attached claims which form a part of this specification.

EXAMPLE 3

Protein G produced from papain treated streptococci

A human group G streptococcal strain, G 148, was cultured in a tryptone medium in a 12 l fermenter. At the end of the logarithmic phase the bacteria were harvested by centrifugation. The biomass yield from a 12 l culture was approximately 100 g (wet weight). Solubilization of Protein G was performed as described by Björck and Kronvall (J Immunol 133 /1984/ p 969-74). Briefly, bacteria were suspended to approximately 10% (w/v) in 10 mM Tris(HCl) pH 8.0. Digestion was carried out by the addition of 100 μ0.4M L-cystein (Sigma) and 80 μg papain (Sigma, P-3125) in the same buffer, per ml bacterial suspension. The mixture was incubated for 1 h at 37° C. on a rotary shaker. The reaction was stopped by the addition of iodoacetamide (Sigma) to a final concentration of 6 mM. The supernatant, approximately 1 l, was recovered by centrifugation. Protein G was isolated from the supernatant by ion exchange chromatography and affinity chromatography.

Ion exchange chromatography; DEAE-Sephacel (Pharmacia AB) 100 ml, was equilibrated in 10 mM Tris(HCl) pH 8.0. The pH of the papain-digerate was adjusted to 8.0 (from pH 5.7) by addition of NaOH, and then the digerate was added to the ion exchanger gel. The slurry was stirred on a rotary shaker for 2 hrs at R.T. After washing with the equilibration buffer on a glass filter, the gel was packed in a K26/40 column (Pharmacia AB). Adsorbed material was eluted by a linear gradient, 500 ml, from 0 to 0.5M NaCl. The Protein G-containing fractions, detected by immunodiffusion (against a polyclonal bovine IgG), were pooled. Affinity chromatography; The Protein G-containing pool, approximately 220 ml, from the ion exchanger, was diluted with an equal volume of PBST (30 mM Na-PO$_4$, 0.12M NaCl pH 7.2, containing 0.05% Tween 20). IgG-Sepharose 4B (Pharmacia AB), 15 ml, was equilibrated in PBST and added to the diluted eluate from the ion exchanger. The slurry was stirred on a rotary shaker for 2.5 hrs at RT. The gel was then washed on a glass filter and packed in a K16/20 column. Desorption of bound material was performed by isocratic elution. The eluent was 0.1M Tris(HCl) pH 2.5 and the flow rate 10 ml/h (5 cm/h). The eluted material was desalted on PD-10 columns (Pharmacia AB) to 30 mM Na-PO$_4$ pH 7.2 $A_{280}$ after the desalting was approximately 1.7/ml and the volume 16 ml.

Results and Discussion

Protein G from papain treated streptococci

A proteolytic enzyme, papain, was used to solubilize Protein G from streptococci. After purification on DEAE-Sephacel and IgG-Sepharose 4B, the Protein G was characterized by analytical chromatography on a Mono Q HR 5/5 column. The appearance of the chromatograms differed considerably depending on how the papain extraction was performed, indicating the difficulties of this solubilization procedure.

If the time of the papain treatment was prolonged the peaks became more numerous and smaller in size. The appearance of the chromatograms also differed considerably depending on the kind and/or batch of papin used. Generally, two main peaks could be seen, which contained the main Protein G activity (as determined by immunodiffusion). Apart from these two peaks, some additional but smaller peaks were seen. The small peaks also contained some Protein G acivity. The appearance of the purified Protein G differed in the same manner when analyzed by SDS-PAGE. In general, it appeared in two main bands with apparent m.w.s.' of about 10 000 and 15 000 respectively. Treatment of the sample with 2-mercaptoethanol did not influence the SDS-PAGE pattern, suggesting that no disulfide bonds are presented in Protein G. Determination of Protein G's isoelectric point was done by IEF. In general, two bands corresponding to pI's of approximately 4.7 and 4.2 were observed. The amino acid composition of the two main fractions of Protein G was determined, revealing a close relationship between the two fractions. The reactivity of Protein G with different antibodies (species and subclasses) was tested by means of immunodiffusion, direct precipitation or inhibition of precipitation. Generally the results show that Protein G precipitates directly with most of the antibodies tested. A weaker interaction (no direct precipitation but ability to inhibit a precipitation) was observed for polyclonal rabbit IgG, one monoclonal mouse IgG1 and one IgG2a. Finally, polyclonal dog, rat and chicken IgG as well as IgM, IgA and IgD from human myelomas, failed to react with Protein G.

Immunization with Protein G 3 rabbits were intramuscularly immunized with a mixture of 250 /μg Protein G and 250 /μg purified sheep IgG in 0.5 ml of saline emulsified with 0.5 ml complete Freunds Adjuvans.

After three consequtive injections during a period of 2 months bleedings of rabbits were regularly performed twice every three week period. Antiserum were collected and tested in immunoelectrophoresis aganist a Protein G preparation prepared as described above, and sheep IgG.

All three rabbits developed strong antiserum reactions against Protein G indicated by precipitate formation. In contrast, sera from the same animals but collected before immunization of Protein G - sheep IgG showed no precipitates.

We claim:

1. In an immunoassay method for the determination of a bacterial polypeptide capable of binding to the Fc-portion of an immunoglobulin, said method comprising the step of performing an immune reaction between said polypeptide and an antibody directed thereagainst, the improvement comprising
   (i) carrying out said immune reaction at a pH-value below 4 at which the immunoglobulin potentially binding to said polypeptide will not substantially bind to said polypeptide,
   (ii) using an antibody preparation that exert antibody-activity at the selected pH below 4 at which the immune reaction is carried out.

2. An immunoassay method according to claim 1 wherein the polypeptide is protein A or portein G.

3. An immunoassay method according to claim 1 wherein the immune reaction is carried out within the pH-range 2.7-3.5.

4. An immunoassay method for the quantitative determination of a bacterial polypeptide capable of binding to the Fc-portion of an immunoglobulin, said method comprising the step of performing an immune reaction at a pH selected in the interval 2.7-4 for the formation of an immune complex containing the polypeptide and an antibody having specificity for said polypeptide,
   (i) the selected pH-value giving no significant binding of the immunoglobulin to the polypeptide, and
   (ii) the antibody being selected so that it will bind to the polypeptide at the pH-value selected.

5. An immunoassay according to claim 1 wherein the polypeptide is protein A.

6. An immunoassay according to claim 4 wherein the polypeptide is protein G.

7. An immunoassay according to claim 4 wherein the pH is selected in the interval 2.7-3.5.

8. An immunoassay method for the quantitative determination of high affinity antibody directed against a bacterial polypeptide capable of binding to the Fc-portion of an immunoglobulin, said method comprising the step of performing an immune reaction at a pH selected in the interval 2.7-4 for the formation of an immune complex containing the bacterial polypeptide and the antibody, the selected pH-value giving no significant binding of the immunoglobulin to the bacerial polypeptide.

9. An immunoassay according to claim 1 wherein the bacterial polypeptide is protein A.

10. An immunoassay according to claim 4 wherein the bacterial polypeptide is protein G.

11. An immunoassay method according to claim 4, wherein the pH is selected in the interval 2.7-3.5.

* * * * *